United States Patent [19]

Schrader

[11] Patent Number: 5,141,488
[45] Date of Patent: Aug. 25, 1992

[54] SLING DEVICE

[76] Inventor: Kenneth L. Schrader, No. 83, 2061 Colley Rd., Beloit, Wis. 53511

[21] Appl. No.: 564,646

[22] Filed: Aug. 9, 1990

[51] Int. Cl.⁵ .................................... A61F 5/01
[52] U.S. Cl. ............................. 602/4; 128/878
[58] Field of Search ............... 128/94, 875, 876, 878

[56] References Cited

U.S. PATENT DOCUMENTS

| | | | |
|---|---|---|---|
| 114,615 | 5/1871 | Smitley | 128/94 |
| 2,111,963 | 3/1938 | Coombs | 128/94 |
| 2,549,703 | 4/1951 | New | 128/94 |
| 2,560,243 | 7/1951 | Peterson | 128/94 |
| 3,108,589 | 10/1963 | Staggs | 128/94 |
| 3,307,538 | 3/1967 | Groll | 128/94 |
| 4,526,164 | 7/1985 | Bihl | 128/94 |
| 4,564,008 | 1/1986 | Donahoo | 128/94 |
| 4,598,702 | 7/1986 | Lilla | 128/94 |
| 4,598,703 | 7/1986 | Lindemann | 128/94 |
| 4,716,895 | 1/1988 | Marques | 128/94 |
| 4,751,923 | 6/1988 | Marino | 128/94 |
| 4,901,713 | 2/1990 | Troeger | 128/94 |

FOREIGN PATENT DOCUMENTS 102473 of 1916 United Kingdom ............... 128/94
2205753 12/1988 United Kingdom.

Primary Examiner—Danton D. DeMille
Assistant Examiner—Kevin G. Rooney
Attorney, Agent, or Firm—David J. Archer

[57] ABSTRACT

A sling device is disclosed for securing to a waistband of a user. The sling device extends over the left and right shoulders of the user for supporting an arm of the user. The device includes a first and second strap extending over the left and right shoulder of the user respectively. Each of the straps has a first and a second end. Front and further front fasteners are connected to the first end of the first and second straps respectively for fastening the first ends of the straps to the waistband. Rear and further fasteners are connected to the second ends of the first and second straps respectively for fastening the second ends to the waistband. A first and second portion each having a first and second extremity are secured at the first extremities to the first and second straps respectively between the front and further front fasteners and the left and right shoulders respectively of the user. Adjustable and further adjustable securing elements are secured to the second extremities of the first and second portions respectively for adjustably securing the second extremities to the first and second portions respectively between the first and second extremities thereof such that the first and second portions define an adjustable loop and a further adjustable loop respectively for adjustably supporting the arm of the user.

5 Claims, 3 Drawing Sheets

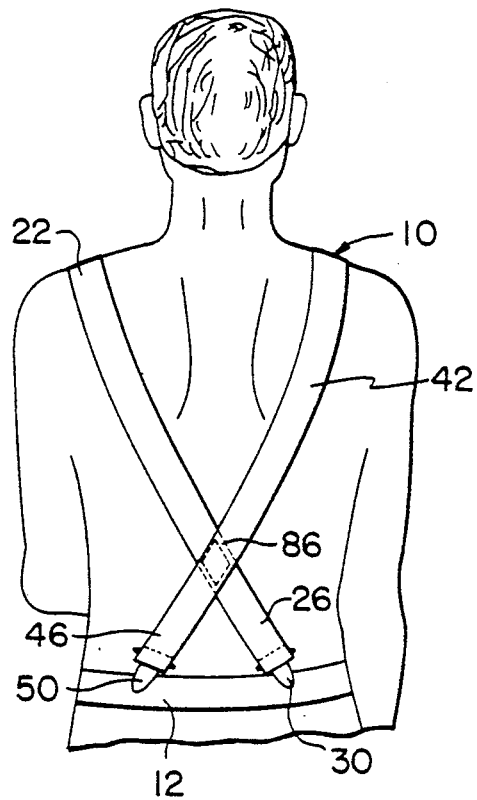
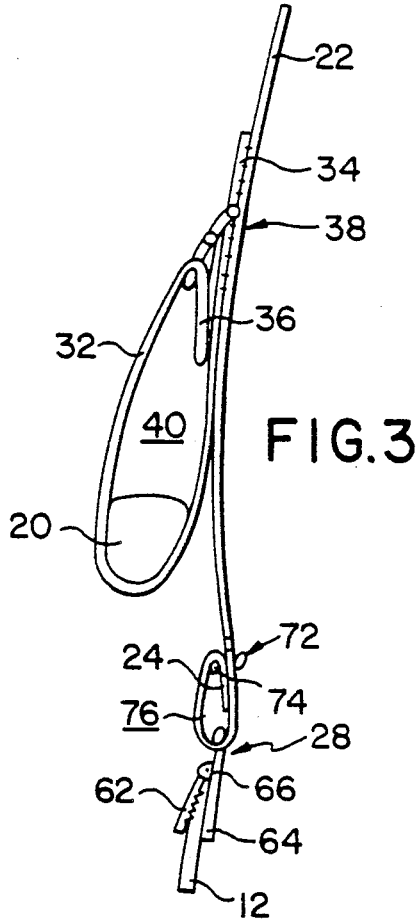
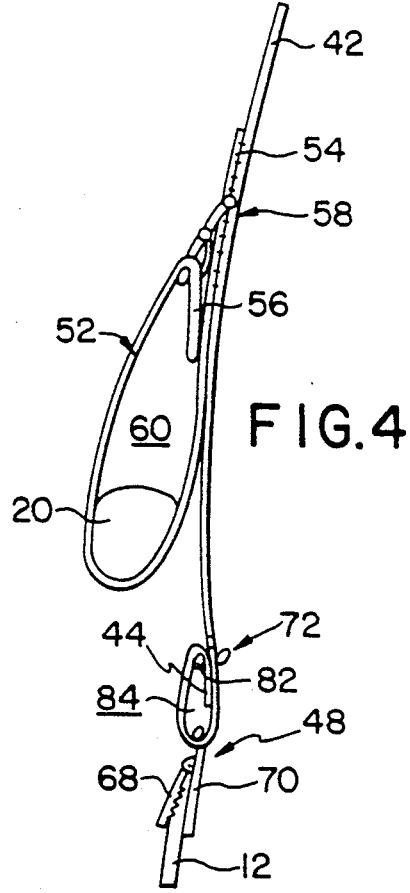

5,141,488

1

SLING DEVICE

BACKGROUND OF THE INVENTION

1. Field of the Invention

The present invention relates to a sling device secured to a waistband of a user for supporting an arm of the user. More particularly, the present invention relates to a sling device secured to a waistband of the user and extending over the left and right shoulder of the user for supporting the arm of the user.

2. Information Disclosure Statement

A broken arm or sprained wrist necessitates support of the patients arm in a position which will prevent strain on the shoulder joint of the patients injured arm.

Typically, sling devices have included a cloth sheet for around the users neck such that the weight of the arm is supported by the users neck. The aforementioned arrangement often causes neck strain to the user.

Furthermore, such prior art sling devices do not facilitate angular adjustment of the lower arm about the elbow joint of the user.

The present invention overcomes the aforementioned problems associated with the prior art sling devices by providing a first and second strap secured to a waistband of the user and a first and second portion adjustably secured to the respective straps for supporting the lower arm of the user at the required angular disposition about the elbow joint of the user.

Therefore it is a primary objective of the present invention to provide a sling device which overcomes the aforementioned inadequacies of the prior art devices and which makes a considerable contribution to the art of surgical slings and the like.

Another objective of the present invention is the provision of a sling device having a first and second strap which extend over the left and right shoulders of the user respectively such that the weight of the users arm is supported by the shoulders of the user rather than the neck of the user thereby inhibiting any tendency to urge the users neck forwardly. Another object of the present invention is the provision of a first and second portion defining respectively an adjustable loop and a further adjustable loop for supporting the lower arm of the user such that the angle between the lower arm and the upper arm of the user can be adjusted thereby providing more comfort for the user.

Other objects and advantages of the present invention will be readily apparent to those skilled in the art by a consideration of the detailed description contained hereinafter taken in conjunction with the annexed drawings.

SUMMARY OF THE INVENTION

The present invention relates to a sling device which is secured to a waistband of the user. The device extends over the left and right shoulders of the user for supporting an arm of the user. The device includes a first strap which extends over the left shoulder of the user with the first strap having a first and a second end. Front fastening means is connected to the first end of the first strap for fastening the first end of the first strap to the waistband. A rear fastening means is connected to the second end of the first strap for fastening the second end of the first strap to the waistband.

A first extremity of a first portion having a first and a second extremity is secured to the first strap between the front fastening means is secured to the second extremity of the first portion for adjustably securing the second extremity to the first portion between the first and second extremities thereof such that the first portion defines an adjustable loop for adjustably supporting the arm of the user.

A second strap extends over the right shoulder of the user, the second strap having a first and second end. A further front fastening means is connected to the first end of the second strap for fastening the first end of the strap to the waistband. Further rear fastening means is connected to the second end of the second strap for fastening the second end of the second strap to the waistband.

A first extremity of a second portion having a first and a second extremity is secured to the second strap between the further front fastening means and the right shoulder of the user. A further adjustable securing means is secured to the second extremity of the second portion for adjustably securing the second extremity of the second portion to the second portion between the first and second extremities of the second portion such that the second portion defines a further adjustable loop for further adjustably supporting the arm of the user.

In a more specific embodiment of the present invention, the straps are of cloth.

Furthermore, the front fastening means further includes a releasable toothed jaw member. A toothed backing member is hingedly secured to the jaw member such that when the jaw member is disposed in a first disposition thereof, the first end of the first strap is connected to the waistband. Also, when the jaw member is disposed in a second disposition thereof, the first end of the first strap is released from the waistband.

Additionally, the further front fastening means also includes a further releasable toothed jaw member and a further toothed backing member. The further toothed backing member is hingedly secured to the further jaw member such that when the further jaw member is disposed in a first disposition thereof, the first end of the second strap is connected to the waistband. Furthermore, when the further jaw member is disposed in a second disposition thereof, the first end of the second strap is released from the waistband.

The sling device also includes adjustable locking means for adjustably locking the front and further front fastening means relative to the first end of the first and second straps respectively.

The adjustable locking means include a first buckle which extends between the first end of the first strap and the first strap between the first end of the first strap and the first extremity of the first portion such that the first strap defines a looped section. The front fastening means slidably engages the first looped section for adjusting the length of the first strap.

The adjustable locking means also includes a second buckle which extends between the first end of the second strap and the second strap between the first end of the second strap and the first extremity of the second portion such that the second strap defines a second looped section. The further front fastening means slidably engages the second looped section for adjusting the length of the second strap.

In a preferred embodiment of the present invention, the first and the second straps cross over each other at a location which is between the first portion and the rear fastening means. The location is also between the second portion and the further rear fastening means.

More specifically, the first and the second straps are secured to each other at the location.

Many modifications and variations of the present invention will be readily apparent to those skilled in the art by a consideration of the detailed description taken in conjunction with the annexed drawings. However, such modifications and variations fall within the spirit and scope of the present invention as defined by the appended claims.

A BRIEF DESCRIPTION OF THE DRAWINGS

FIG. 1 is a front elevational view of a sling device according to the present invention;

FIG. 2. is a rear elevational view of the sling device shown in FIG. 1; FIG. 3. is an enlarged sectional view taken on the line 33 3 of FIG. 1. showing an adjustable loop for adjustably supporting the arm of the user.

FIG. 4 is an enlarged sectional view taken on the line 4-4 of FIG. 1. showing a further adjustable loop for adjustably supporting the arm of the user;

FIG. 5. is an enlarged sectional view taken on the line 5-5 of FIG. 1, but shows the front fastening means in a second disposition thereof;

FIG. 6. is an enlarged sectional view taken on the line 6-6 of FIG. 1, but shows the further front fastening means in a second disposition thereof; and, FIG. 7. is a front elevational view of a further embodiment of the present invention.

Similar reference characters refer to similar parts throughout the various embodiments shown in the drawings.

DETAILED DESCRIPTION OF THE DRAWINGS

Figure 1:
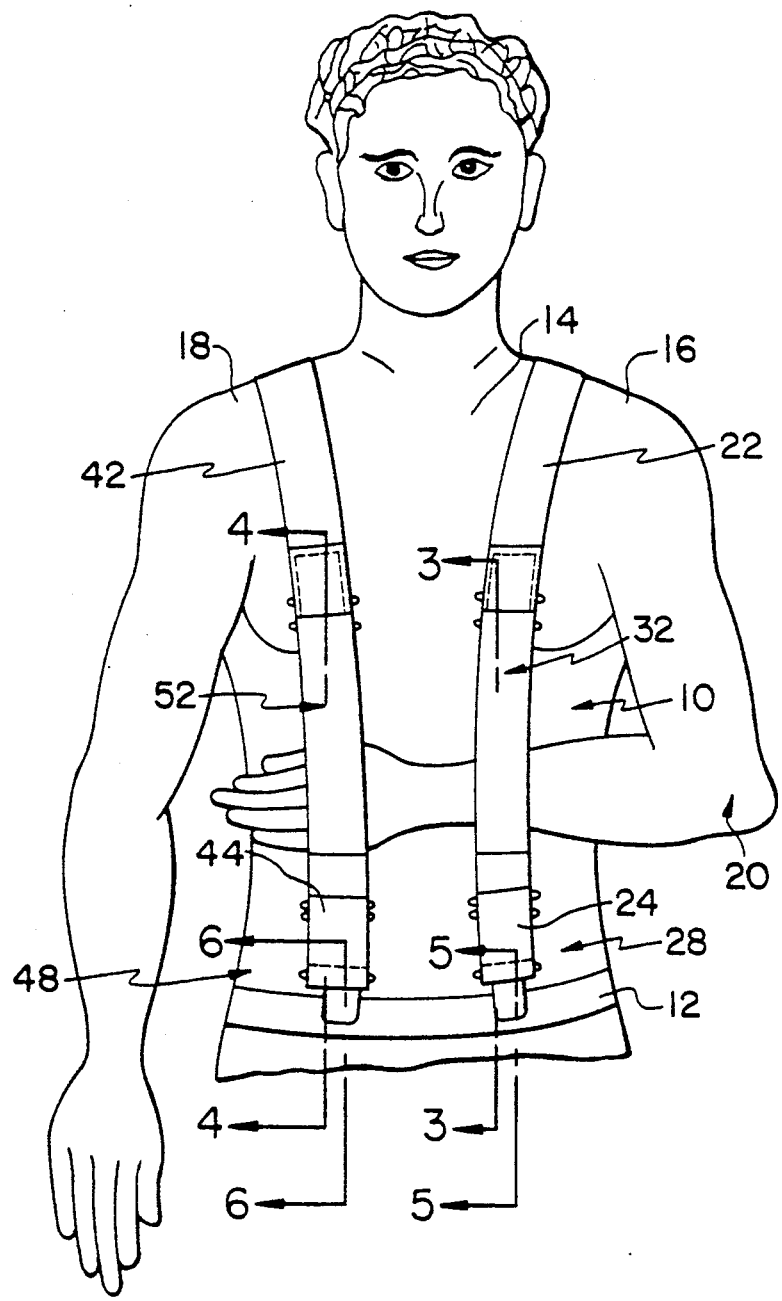

FIG. 1. is a front elevational view of a sling device generally designated 10 according to the present invention. The sling device 10 is secured to a waistband 12 of a user 14. The device 10 extends over a left and right shoulder 16 & 18 of the user 14 for supporting an arm 20 of the user 14.

The device 10 includes a first strap 22 which extends over the left shoulder 16 of the user 14. The first strap 22 has a first and a second end 24 & 26, respectively as shown in FIG. 2.

Front fastening means generally designated 28 is connected to the first end 24 of the first strap 22 for fastening the first end 24 of the first strap 22 to the waistband 12.

Rear fastening means 30 is connected to the second end 26 of the first strap 22 for fastening the second end 26 of the first strap 22 to the waistband 12

FIG. 3 is a sectional view taken on the line 3—3 of FIG. 1. FIG. 3 shows a first portion generally designated 32 having a first and a second extremity 34 & 36 respectively. The first extremity 34 is secured to the first strap 22 between the front fastening means 28 and the left shoulder 16 of the user 14.

An adjustable securing means designated 38 is secured to the second extremity 36 of the first portion 32 for adjustably securing the second extremity 36 to the first portion 32 between the first and second extremities 34 & 36 respectively. The arrangement is such that the first portion 32 defines an adjustable loop 40 for adjustably supporting the arm 20 of the user 14.

A second strap 42 extends over the right shoulder 18 of the user 14. The second strap 42 has a first and a second end 44 & 46.

Further front fastening means generally designated 48 is connected to the first end 44 of the second strap 42 for fastening the first end 44 of the second strap 42 to the waistband 12.

Further rear fastening means 50 is connected to the second end 46 of the second strap 42 for fastening the second end 46 of the second strap 42 to the waistband 12.

FIG. 4 is a sectional view on the line 4-4 of FIG. 1 and shows a second portion generally designated 52 which has a first and second extremity 54 and 56 respectively. The first extremity 54 of the second portion 52 is secured to the second strap 42 between the further front fastening means 48 and the right shoulder 18.

A further adjustable securing means generally designated 58 is secured to the second extremity 56 of the second portion 52 for adjustably securing the second extremity 56 of the second portion 52 to the second portion 52 between the first and second extremities 54 & 56 respectively of the second portion 52 such that the second portion 52 defines a further adjustable loop 60 for further adjustably supporting the arm 20 of the user 14.

In a preferred embodiment of the present invention, the straps 22 & 42 are of cloth.

Figure 5:
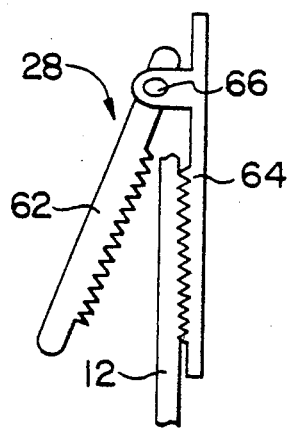

The front fastening means 28 also includes a releasable toothed jaw member 62 and a toothed backing member 64 hingedly secured to the jaw member 62 at 66 such that when the jaw member 62 is disposed in a first position thereof as shown in FIG. 1, the first end 24 of the first strap 22 is connected to the waistband 12 and when the jaw member 62 is disposed in a second disposition thereof as shown in FIG. 5, the first end 24 of the first strap 22 is released from the waistband 12.

Figure 6:
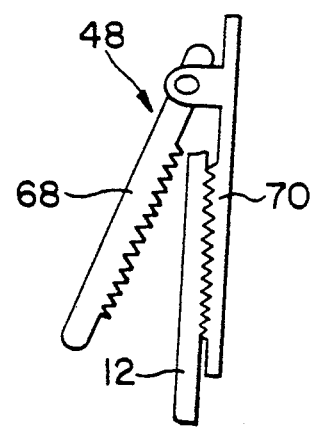

The further front fastening means 48 also includes a further releasable toothed jaw member 68 as shown in FIG. 6. and a further toothed backing member 70 such that when the further jaw member 68 is disposed in a first disposition thereof as shown in FIG. 1, the first end 44 of the second strap 42 is connected to the waistband 12 and when the further jaw member 68 is disposed in a second disposition thereof as shown in FIG. 6, the first end 44 of the second strap 42 is released from the waistband 12.

An adjustable locking means generally designated 72 shown in FIGS. 3 and 4 adjustably locks the front and further front fastening means 28 and 48 respectively relative to the first ends 24 and 44 of the first and second straps 22 and 42 respectively. The adjustable locking means 72 includes a first buckle 74. which extends between the first end 24 of the first strap 22 and the first strap 22 between the first end 24 of the first strap 22 and the first extremity 34 of the first portion 32, such that the first strap 22 defines a first looped section 76. The front fastening means 28 slidably engages the first looped section 76 for adjusting the length of the first strap 22.

The adjustable locking means 72 also includes a second buckle 82 shown in FIG. 4 which extends between the first end 44 of the second strap 42 and the second strap 42 between the first end 44 of the second strap 42 and the first extremity 54 of the second portion 52 such that the second strap 42 defines a second looped section 84. The further front fastening means 48 slidably engages the second looped section 84 for adjusting the length of the second strap 42.

FIG. 2. is a rear elevational view of the sling device 10. shown in FIG. 1. FIG. 2. shows the first and second straps 22 & 42 respectively crossing over each other at a location 86 which is between the first portion 32 and the rear fastening means 30 and between the second portion 52 and the further rear fastening means 50. More particularly, as 1 shown in FIG. 2. the first and second straps 22 & 42 respectively are secured to each other at the location 86 as by stitching or the like.

Figure 7:
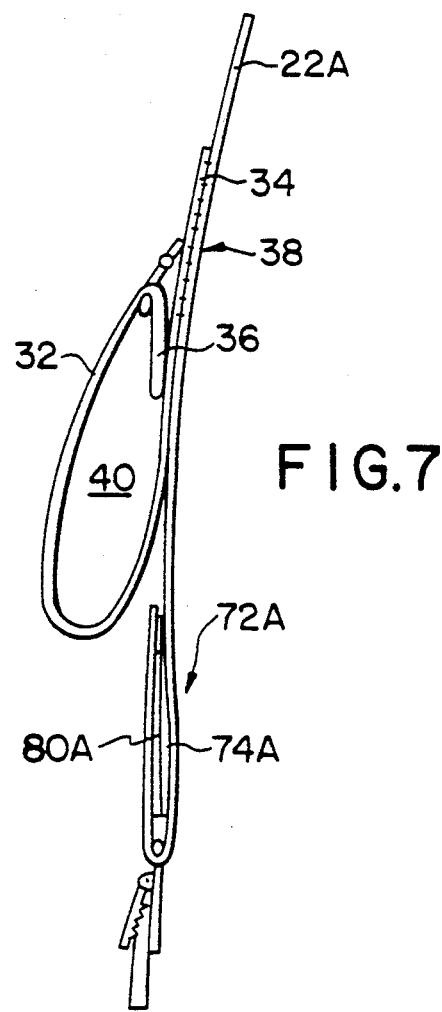

FIG. 7 is an enlarged side elevational view showing a further embodiment of the present invention in which adjustable locking means generally designated 72A include a first and second VELCRO strip 74A & 80A respectively fastened to the first strap 22A as shown and second strap 42A (not shown). for permitting adjustments to the lengths of the straps. VELCRO is a Registered Trade Mark of American VELCRO Inc. of Manchester N.H.

In operation of the device in either embodiment of the present invention, the user places the injured arm through the adjustable & further adjustable loops and adjusts the position of the loop and further loop until the user attains the required angular disposition of the injured arm.

The present invention provides a sling device which not only supports the arm of the user from the users shoulders, but also enables the user to adjust the angular position of the users lower arm relative to the upper arm thereby making the sling more comfortable.

What is claimed is:

1. A sling device secured to a waistband of a user and extending over a left and right shoulder of the user for supporting an arm of the user, said device comprising:
    a first strap adapted to extend over the left shoulder of the user, said first strap having a first and second end;
    front fastening means connected to said first end of said first strap for adjustably fastening said first end of said first strap to the waistband;
    rear fastening means connected to said second end of said first strap for fastening said second end of said first strap to the waistband;
    a first portion having a first and a second extremity, said first extremity during use of the device being secured to said first strap between said front fastening means and the midpoint of said first strap;
    an adjustable securing means secured to said second extremity of said first portion for adjustably securing said second extremity to said first portion between said first and second extremities thereof such that said first portion defines an adjustable loop for adjustably supporting the arm of the user;
    a second strap adapted to extend over the right shoulder of the user, said second strap having a first and second end;
    further front fastening means connected to said first end of said second strap for adjustably fastening said first end of said second strap to the waistband;
    further rear fastening means connected to said second end of said second strap for fastening said second end of said second strap to the waistband;
    a second portion having a first and a second extremity, said first extremity of said second portion in use of the device being secured to said second strap between said further front fastening means and the midpoint of said second strap;
    a further adjustable securing means secured to said second extremity of said second portion for adjustably securing said second extremity of said second portion to said second portion between said first and second extremities of said second portion such that said second portion defines a further adjustable loop for further adjustably supporting the arm of the user;
    said first and second strap crossing over each other at a location which is between said first portion and said rear fastening means and which is between said second portion and said further rear fastening means; and
    said first and second straps being secured to each other at said location, the arrangement begin such that in use of the device, when said front and said further front fastening means are adjusted, the height of the waistband relative to the shoulders of the user is altered without appreciably altering a distance between said adjustable loop and the left shoulder of the user and a further distance between said further adjustable loop and the right shoulder of the user so that adjustment of the height of the waistband does not appreciably alter the disposition of the arm of the user.

2. A sling device as set forth in claim 1 wherein said straps are of cloth.

3. A sling device as set forth in claim 1 wherein said front fastening means further includes;
    a releasable toothed jaw member;
    a releasable toothed backing member hingedly secured to said jaw member such that when said jaw member is disposed in a first disposition thereof, said first end of said first strap is connected to the waistband and when said jaw member is disposed in a second disposition thereof, said first end of said first strap is released from the waistband;
    said further front fastening means further including :
    a further releasable toothed jaw member;
    a further toothed backing member hingedly secured to said further jaw member such that when said further jaw member is disposed in a first disposition thereof, said first end of said second strap is connected to the waistband and when said further jaw member is disposed in a second disposition thereof, said first end of said second strap is released from the waistband.

4. A sling device as set forth in claim 1 further including:
    adjustable locking means for adjustably locking said front and said further front fastening means relative to said first ends of said first and second straps respectively.

5. A sling device as set forth in claim 4 wherein said adjustable locking means includes :
    a first buckle extending between said first end of said first strap and said first strap between said first end of said first strap and said first extremity of said first portion such that said first strap defines a first looped section, said front fastening means slidably engaging said first looped section for adjusting the length of said first strap;
    a second buckle extending between said first end of said second strap and said second strap between said first end of said second strap and said first extremity of said second portion such that said second strap defines a second looped section, said further front fastening means slidably engaging said second looped section for adjusting the length of said second strap;

* * * * *